(12) United States Patent
Gill et al.

(10) Patent No.: US 7,289,847 B1
(45) Date of Patent: Oct. 30, 2007

(54) IMPLANTABLE CARDIAC DEVICE AND METHOD OF TREATING ATRIAL FIBRILLATION

(75) Inventors: Jong Gill, Valencia, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 250 days.

(21) Appl. No.: 11/038,553

(22) Filed: Jan. 18, 2005

(51) Int. Cl.
*A61N 1/05* (2006.01)

(52) U.S. Cl. .................. 607/5; 607/3; 607/4; 607/14

(58) Field of Classification Search ............. 607/3–5, 607/14
See application file for complete search history.

(56) References Cited

U.S. PATENT DOCUMENTS

| | | | |
|---|---|---|---|
| 4,686,988 A | 8/1987 | Sholder | 128/419 PT |
| 4,708,142 A | 11/1987 | DeCote, Jr. | 128/419 PT |
| 4,712,555 A | 12/1987 | Thornander et al. | 128/419 PG |
| 4,729,376 A | 3/1988 | DeCote, Jr. | 128/419 PT |
| 4,788,980 A | 12/1988 | Mann et al. | 128/419 PG |
| 4,809,697 A | 3/1989 | Causey, III et al. | 128/419 PT |
| 4,940,052 A | 7/1990 | Mann et al. | 128/419 PG |
| 4,944,298 A | 7/1990 | Sholder | 128/419 PG |
| 4,944,299 A | 7/1990 | Silvian | 128/419 PG |
| 4,969,467 A | 11/1990 | Callaghan et al. | 128/419 PG |
| 5,350,410 A | 9/1994 | Kleks et al. | 607/28 |
| 5,549,641 A * | 8/1996 | Ayers et al. | 607/4 |
| 5,562,708 A | 10/1996 | Combs et al. | 607/4 |
| 5,674,251 A | 10/1997 | Combs et al. | 607/4 |
| 5,814,079 A * | 9/1998 | Kieval | 607/4 |
| 6,078,837 A | 6/2000 | Peterson et al. | 607/14 |
| 6,178,351 B1 | 1/2001 | Mower | 607/5 |
| 6,275,734 B1 | 8/2001 | McClure et al. | 607/27 |
| 6,337,995 B1 | 1/2002 | Mower | 607/5 |
| 6,484,057 B2 | 11/2002 | Ideker et al. | 607/14 |
| 2002/0123771 A1 | 9/2002 | Ideker et al. | 607/14 |
| 2003/0032986 A1 | 2/2003 | Kupper | 607/5 |
| 2003/0153951 A1 * | 8/2003 | Ideker et al. | 607/3 |

FOREIGN PATENT DOCUMENTS

| | | |
|---|---|---|
| EP | 1 146 929 B1 | 7/2004 |
| WO | WO95/28987 | 11/1995 |

OTHER PUBLICATIONS

Wells, J., "Characterization of Atrial Fibrillation in Man: Studies Following Open Heart Surgery," PACE, vol. 1 (Oct.-Dec. 1978), pp. 426-438.

* cited by examiner

*Primary Examiner*—Carl Layno
*Assistant Examiner*—Deborah Malamud

(57) ABSTRACT

An apparatus and method of treating atrial fibrillation (AF) are provided. The apparatus includes means for detecting AF in a heart of a patient, means for classifying the AF as one of a plurality of AF types, means for selecting a therapy for delivery to the heart, from a plurality of therapies, based on AF type, and means for delivering the selected therapy to the heart. The plurality of therapies includes ATP therapy, a hybrid therapy including a combination of ATP therapy and drug therapy, and shock therapy. The method includes sensing an electrogram signal from the heart, analyzing the electrogram signal to detect AF in the heart, classifying the AF as one of a plurality of AF types, selecting a therapy for delivery to the heart, from a plurality of therapies, based on the AF type, and delivering the selected therapy to the heart.

15 Claims, 6 Drawing Sheets

TYPE I  $A_{EG}$  A

TYPE II  $A_{EG}$  B

TYPE III  $A_{EG}$  C

TYPE IV  $A_{EG}$  D

IMPLANTABLE CARDIAC DEVICE AND METHOD OF TREATING ATRIAL FIBRILLATION

FIELD OF THE INVENTION

The present invention relates generally to implantable cardiac devices. More specifically, the present invention relates to an implantable cardiac device and method of treating atrial fibrillation.

BACKGROUND

Atrial fibrillation (AF) has typically been treated using shock therapy. When a patient's heart is found to be in AF, a jolting electrical pulse, or shock pulse, is delivered to the patient in order to reactivate the electrical signals throughout the heart. The shock pulse may be administered via external defibrillators, or via implantable cardiac device (ICDs) configured to deliver such a shock. Patients, however, feel uncomfortable using shock therapy because of the pain and discomfort associated with the shock. This is particularly the case if the shock therapy is applied frequently due to the reoccurring nature of AF.

Pacing therapies, such as anti-tachycardia pacing (ATP), have been proposed for the treatment of AF. Pacing therapy, if successful, is preferred over shock therapy since pacing therapy is relatively pain free and saves battery consumption. ATP therapies used to treat AF generally consist of "underdrive" pacing and "overdrive" pacing. Underdrive pacing is when the heart is paced at a rate slower than the arrhythmia rate. Overdrive pacing is when the heart is paced at a rate faster than the arrhythmia rate. Subsequently, overdrive pacing consists of various forms of pacing; i.e. scanning burst, shifting bursts, ramp pacing, etc.

Even though significant progress has been made with pacing therapy, however, it is still limited primarily to the prevention of AF and termination of atrial flutter. If AF can be terminated with pacing therapy, with or without pharmacological assistance, it will be a significant improvement in the treatment of AF.

For successful treatment of AF, an important aspect is whether the cardiac tissue can be captured. When cardiac tissue is captured, a temporary conduction block zone is created, which hinders conduction of fibrillatory wave propagation. If enough of these conductive blocks are created, fibrillatory waves will run out of tissue to propagate, thus extinguishing arrhythmia. Recent studies have found that AF can be classified as one of four types, with certain types being more capturable than others. Further research suggests that atrial tissue can be captured, and more specifically, atrial tissue in Type I AF or Type II AF is more likely to be captured than Type III AF or Type IV AF.

In "Characterization of Atrial Fibrillation in Man: Studies Following Open Heart Surgery," by J. Wells, *PACE*, Vol. 1, 1978, which is hereby incorporated by reference, Wells classified AF according to electrogram (EGM) morphologies. Type I AF represents discrete organized atrial EGMs with intervening isoelectric lines free of perturbation. Type II AF also represents discrete organized atrial EGMs, but without clear isoelectric intervals. Type III AF has disorganized atrial EGMs, without clear isoelectric intervals. Type IV AF is characterized as alternations between Type I AF and Type III AF.

SUMMARY

In accordance with one embodiment, there is provided an implantable cardiac device (ICD) operative to detect atrial fibrillation (AF) in a heart of a patient, classify the AF as one of a plurality of AF types, select a therapy for delivery to the heart, from a plurality of therapies, based on AF type, and deliver the selected therapy to the heart. The plurality of therapies includes anti-tachycardia pacing (ATP) therapy, a hybrid therapy including a combination of ATP therapy and drug therapy, and shock therapy.

In accordance with another embodiment, there is provided an ICD comprising a sense circuit, a processor coupled to the sense circuit, and a therapy circuit. The sense circuit functions to sense an electrocardiogram (EGM) signal from the heart. The processor functions to analyze the EGM signal, detect AF, classify the AF by type, and select a therapy based on the AF type. The therapy circuit is responsive to the processor, and delivers the selected therapy to the heart. The selected therapy can be ATP therapy, a hybrid therapy including a combination of ATP therapy and drug therapy, or shock therapy. The processor is also configured to determine if the selected therapy successfully terminated the AF. If termination was unsuccessful, the therapy circuit is configured to switch to a more aggressive therapy.

In accordance with yet another embodiment, there is provided a method of treating AF. The method includes sensing an electrogram signal from the heart, analyzing the electrogram signal to detect AF in the heart, classifying the AF as one of a plurality of AF types, selecting a therapy for delivery to the heart, from a plurality of therapies, based on the AF type, and delivering the selected therapy to the heart. The plurality of therapies includes ATP therapy, a hybrid therapy including a combination of ATP therapy and drug therapy, and shock therapy.

BRIEF DESCRIPTION OF THE FIGURES

The accompanying figures, which are incorporated herein and form part of the specification, illustrate an example embodiment and, together with the description, further serve to enable a person skilled in the relevant art(s) to make and use the invention. In the figures, like reference numbers indicate identical or functionally similar elements.

DETAILED DESCRIPTION

The following detailed description refers to the accompanying figures that illustrate exemplary embodiments. Other embodiments are possible, and modifications may be made to the embodiments within the spirit and scope of the appended claims. For example, it would be apparent to one of skill in the art that, as described below, many different embodiments of hardware, software, firmware, and/or the entities illustrated in the figures may be implemented. Any actual software and/or hardware described herein is not meant to be limiting. The accompanying description is presented with the understanding that modifications and variations of the embodiments are possible, given the level of detail presented herein. Therefore, the following detailed description is not meant to be limiting in any way; rather, the scope of the invention is defined by the appended claims.

Before describing the embodiments illustrated in the accompanying figures, it is helpful to describe an example environment in which such embodiments may be implemented. Such an example environment is an implantable cardiac device (ICD). An ICD is a medical device that is implanted in a patient to monitor electrical activity of a heart and to deliver appropriate electrical therapy; for example, pacing pulses, cardioverting pulses, or defibrillating (or shock) pulses, as required. ICDs include, for example, pacemakers, cardioverters, defibrillators, implantable cardioverter defibrillators, and the like. The term "implantable cardiac device" or simply "ICD" is used herein to refer to any implantable cardiac device.

Figure 1:
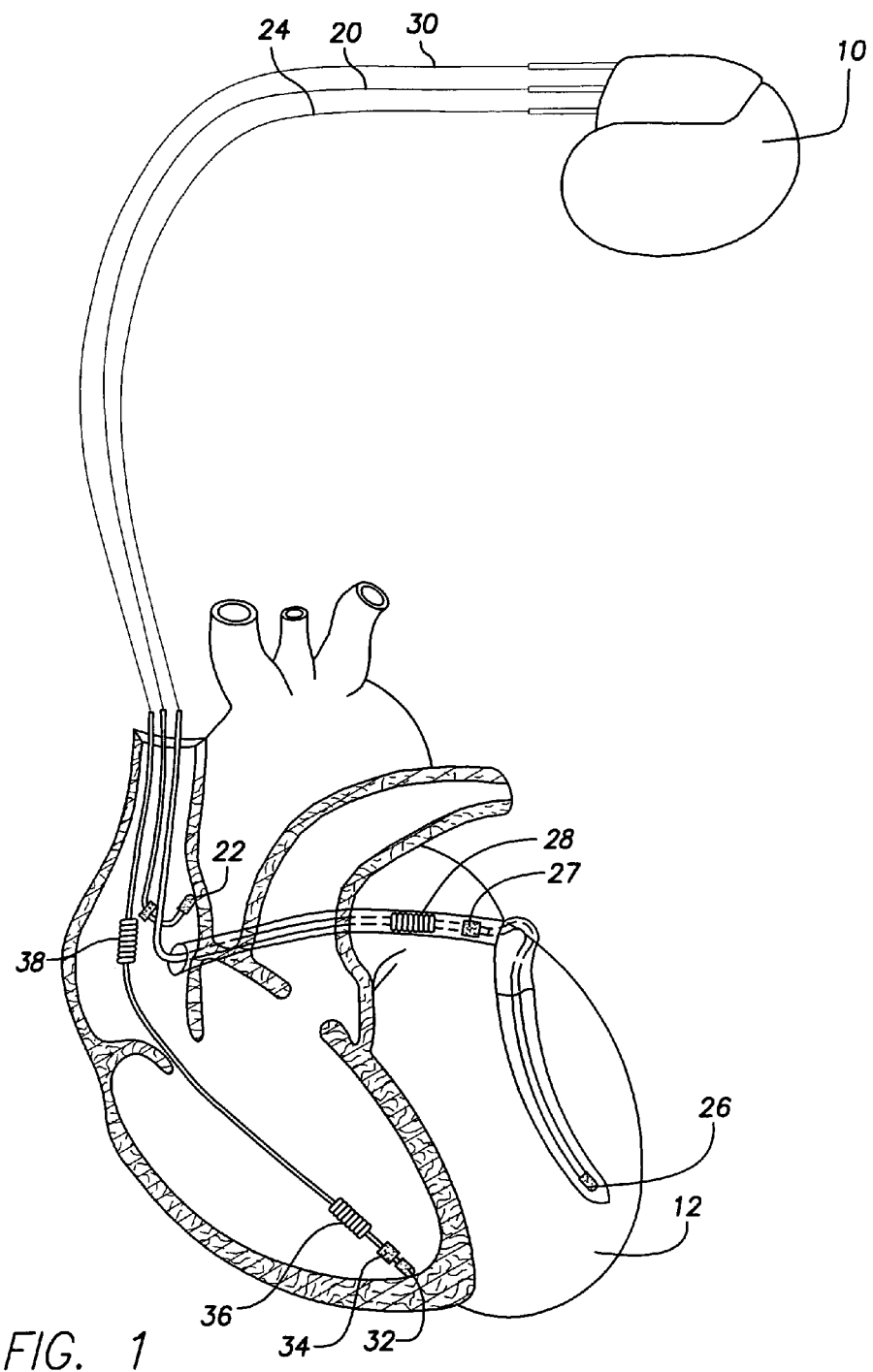
FIG. 1 is a simplified diagram illustrating an exemplary ICD in electrical communication with a patient's heart by means of three leads suitable for delivering multi-chamber stimulation and pacing therapy.

FIG. 1 illustrates an exemplary ICD 10 in electrical communication with a patient's heart 12 by way of three leads 20, 24 and 30, suitable for delivering multi-chamber stimulation and pacing therapy. To sense atrial cardiac signals, and to provide right atrial chamber stimulation therapy, ICD 10 is coupled to implantable right atrial lead 20, having at least an atrial tip electrode 22, which typically is implanted in the patient's right atrial appendage.

To sense left atrial and ventricular cardiac signals, and to provide left-chamber pacing therapy, ICD 10 is coupled to "coronary sinus" lead 24. Lead 24 is designed for placement in the "coronary sinus region," via the coronary sinus, for positioning of a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein, or any other cardiac vein accessible by the coronary sinus. Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shock therapy using at least a left atrial coil electrode 28.

ICD 10 is also shown in electrical communication with the patient's heart 12 by way of an implantable right ventricular (RV) lead 30 having, in this embodiment, a RV tip electrode 32, a RV ring electrode 34, a RV coil electrode 36, and a superior vena cava (SVC) coil electrode 38. Typically, RV lead 30 is transvenously inserted into heart 12 so as to place the RV tip electrode 32 in the right ventricular apex so that RV coil electrode 36 will be positioned in the RV and SVC coil electrode 38 will be positioned in the SVC. Accordingly, RV lead 30 is capable of receiving cardiac signals and delivering stimulation in the form of pacing and shock therapy to the right ventricle.

Amongst other things, leads 20, 24, and 30 function as a sense circuit to sense an electrogram (EGM) signal from the heart 12. The EGM is then processed within the ICD 10 processor (not shown), as discussed below. The leads 20, 24, and 30, and processor (not shown), thereby serve as a means for detecting atrial fibrillation (AF) in the patient's heart 12. As will be further discussed below, the processor also serves as a means for classifying the AF, by analyzing the EGM morphologies and classifying the AF by type; i.e. Type I AF, Type II AF, Type III AF, or Type IV AF. The processor also serves as a means for selecting a therapy for delivery to the heart, from a plurality of therapies, based on the AF type. Finally, the leads 20, 24, and 30, in part, serve as delivering means, to thereby deliver the selected therapy to the heart.

The selected therapy can be, but is not limited to, ATP therapy, a hybrid therapy including a combination of ATP therapy and drug therapy, or shock therapy. If ATP therapy is selected, a series of burst pulses is sent to the heart through any one of leads 20, 24, and 30, or any combination thereof. Burst pulses consist of electrical pulses of variable amplitude. Exemplary values of amplitude range from 0-4.0 V, in steps of 0.25 V, or 4.5-7.5 V, in steps of 0.5 V. The pulse width is also variable. Exemplary values of pulse width for ATP range from 0.1-1.5 msec, in 0.05 msec steps. If a hybrid therapy is necessary, a variety of drug delivery means can be employed; i.e. intravenous administration, oral administration, implantable drug delivery means, or any other drug delivery means known in the art. Any drug, known in the art to effectuate cardiac tissue capture may be appropriate; for example dofetilide, or any other class I or class III drugs.

Figure 2:
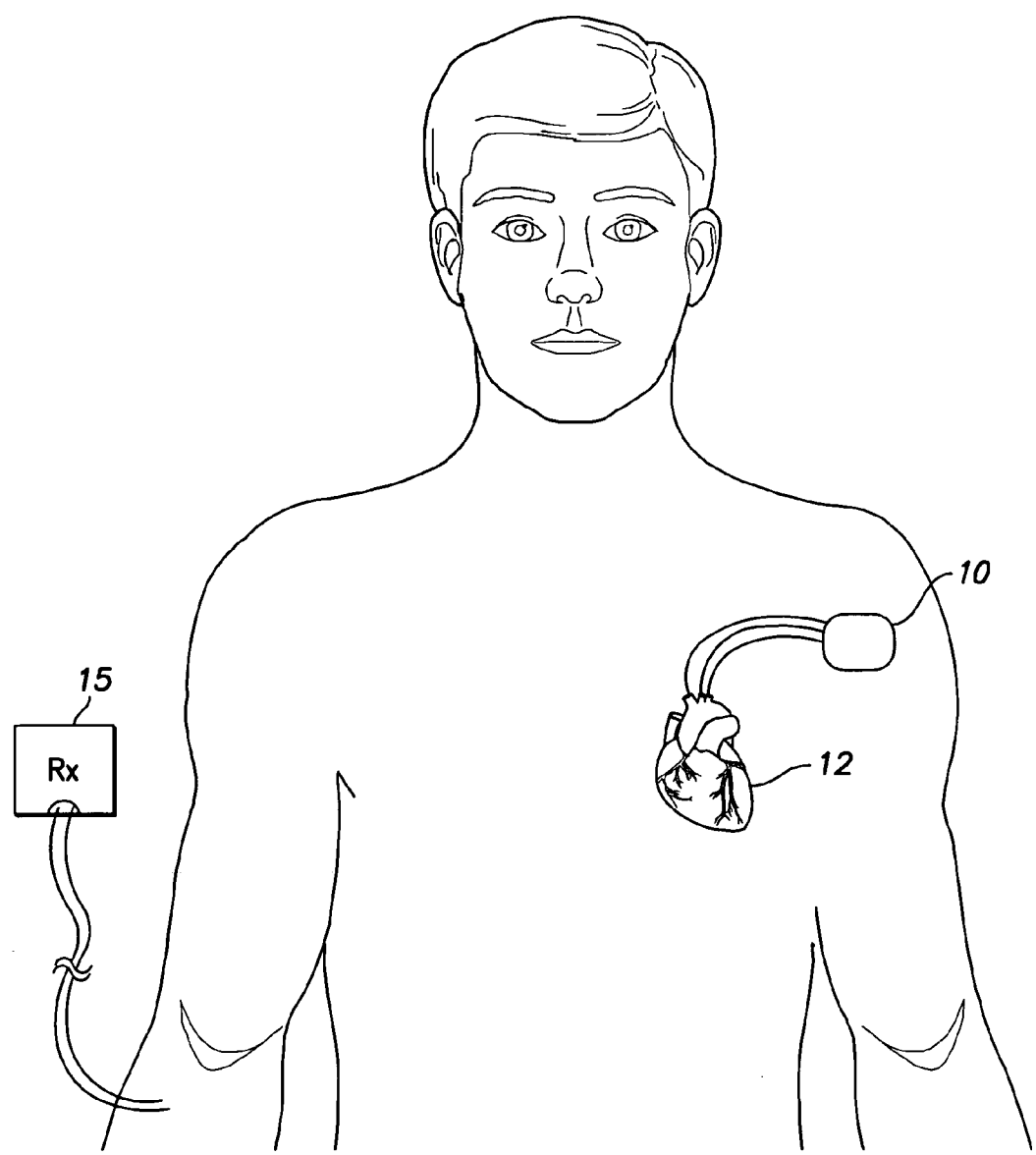
FIG. 2 is a schematic drawing of the ICD of FIG. 1, wherein a drug therapy is administered intravenously.

FIG. 2 is a schematic drawing of the ICD 10, implanted within a patient, and an intravenous drug delivery means for administration of a pharmacological (drug) agent. As shown, the ICD 10 is implanted in a patient, and electrically coupled to the patient's heart 12, as discussed with respect to FIG. 1. The patient is also connected to drug delivery means 15. In one embodiment, drug delivery means 15 can include intravenous delivery of a drug (as shown). In an alternative embodiment, the patient can have the drugs administered through an oral drug delivery means (not shown). In the embodiment shown, if the ICD 10 analyzes the EGM and determines that a hybrid therapy is appropriate, and thus drug delivery is necessary, the ICD must include a notification means to alert the patient, or caretaker, of the need to administer a drug. Notification means could comprise of a vibration circuit within the ICD 10, a beeping sound, a telemetric signal to an external device, or any other notification means known to the art.

Figure 3:
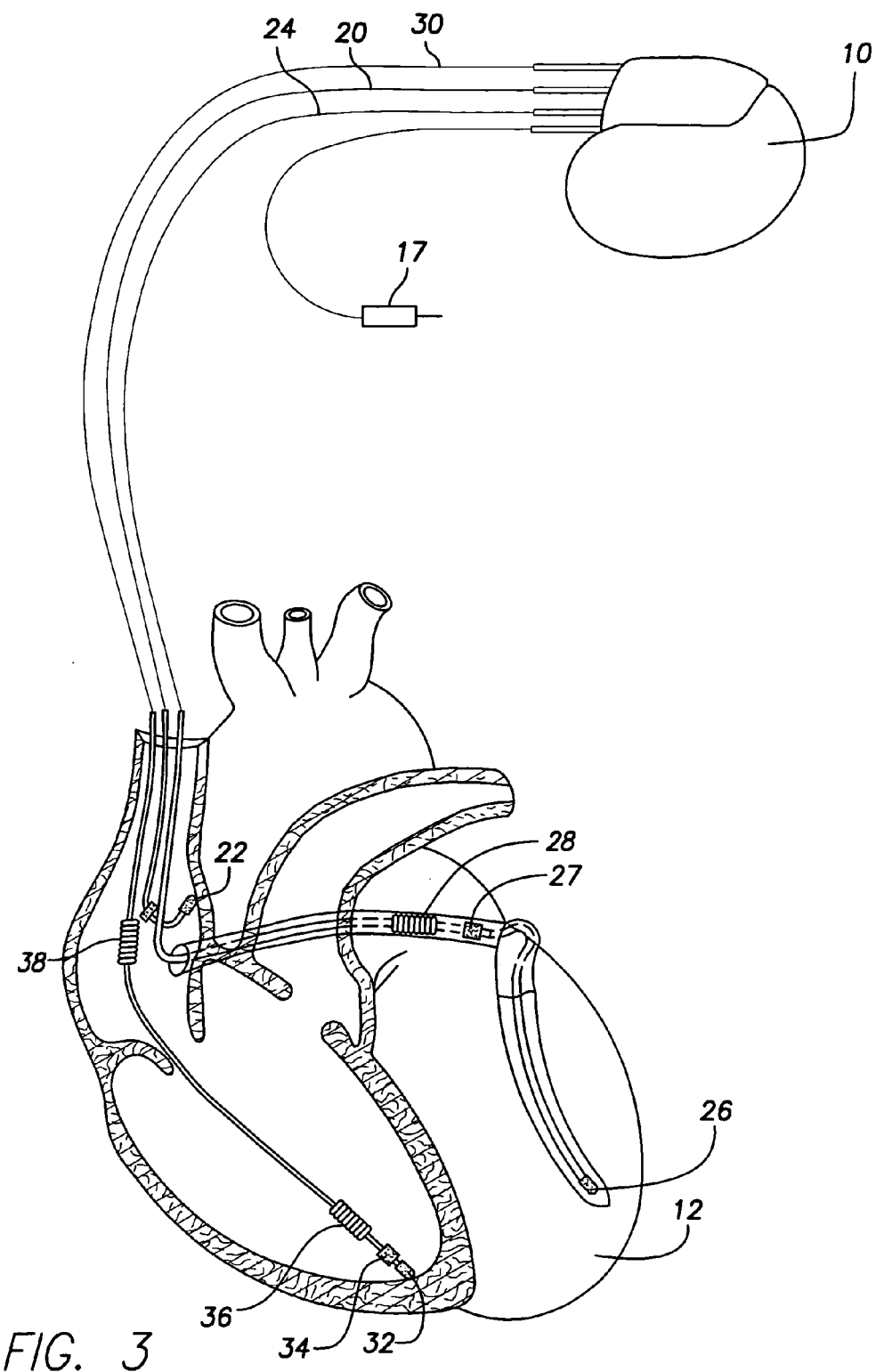
FIG. 3 is a simplified diagram illustrating an exemplary ICD in electrical communication with the patient's heart by means of three leads suitable for delivering multi-chamber stimulation and pacing therapy. The ICD of FIG. 3 shows an implantable drug delivery means.

FIG. 3 illustrates an alternative embodiment, wherein ICD 10 is directly coupled to an implantable drug storage unit 17. The implantable drug storage unit 17 is configured to deliver an appropriate drug to the patient. As such, if a hybrid therapy is selected, the ICD 10 can directly and automatically initiate administration of the appropriate drug. Such an embodiment may provide more efficient control of the timing and quantity of drugs delivered to the patient. Furthermore, such drug delivery means may remove the need for an external notification system.

Figure 4:
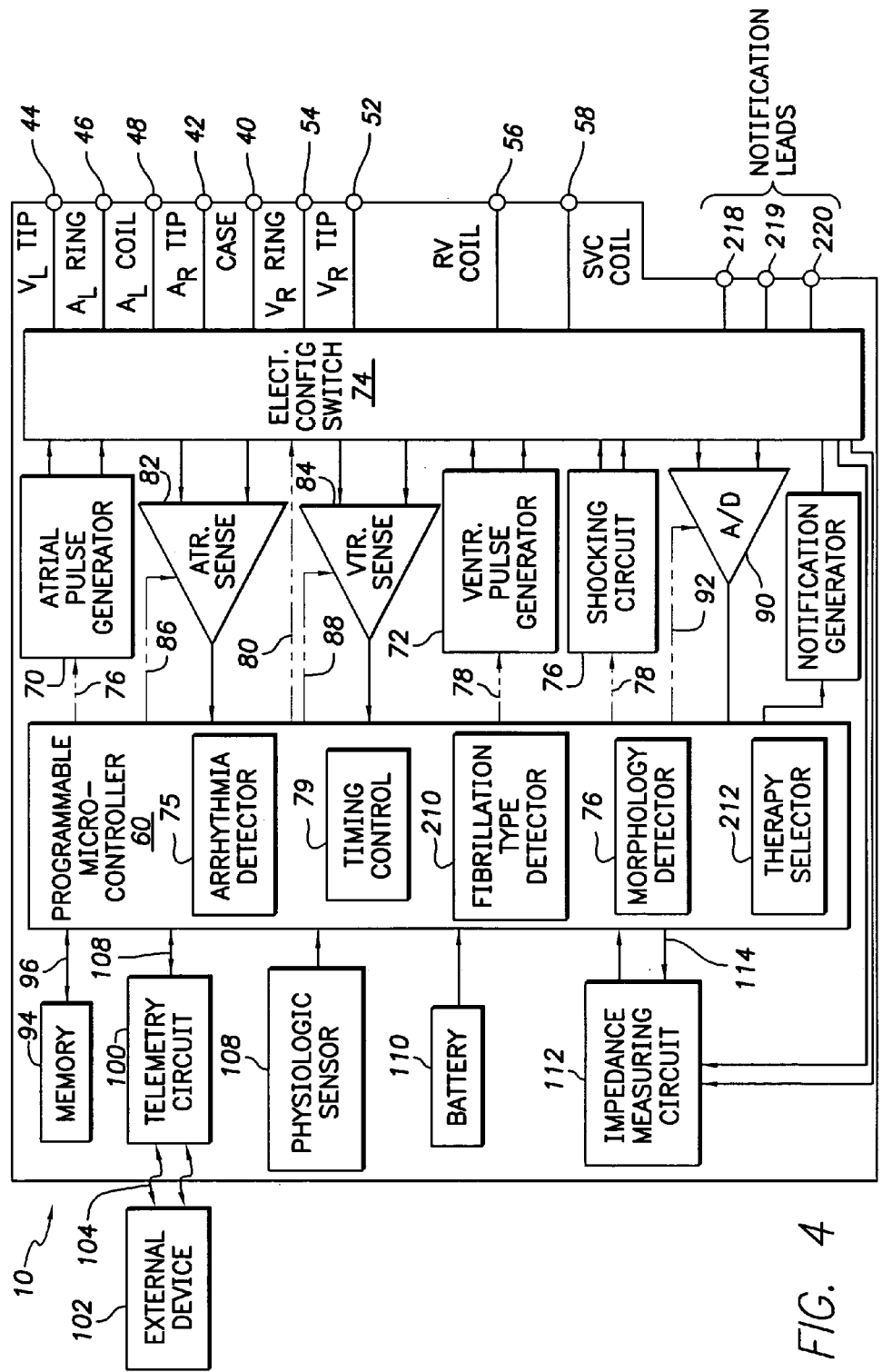
FIG. 4 is a functional block diagram of an exemplary ICD that can provide, amongst other things, cardioversion, defibrillation, and pacing stimulation in three chambers of a heart.
Figure 5:
FIGS. 5A-5D show examples of electrogram signals classified as Type I AF, Type II AF, Type III AF, and Type IV AF, respectively.
Figure 5:
Figure 5:
Figure 5:

FIG. 4 shows a simplified block diagram of ICD 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of ICD 10, shown schematically in FIG. 4, is often referred to as the "can," "case" or "case electrode" and may be programmably selected to act as the return electrode for all "unipolar" modes. Housing 40 may further be used as a return electrode alone or in combination with one or more of coil electrodes 28, 36, and 38, for shocking purposes. Housing 40 further includes a connector (not shown) having a plurality of terminals 42, 44, 46, 48, 52, 54, 56, 58, 218, 219, and 220 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to atrial tip electrode 22.

To achieve left chamber sensing, pacing, and shocking, the connector includes at least a left ventricular tip terminal (VL TIP) 44, a left atrial ring terminal (AL RING) 46, and a left atrial shocking terminal (AL COIL) 48, which are adapted for connection to left ventricular ring electrode 26, left atrial tip electrode 27, and left atrial coil electrode 28, respectively.

To support right chamber sensing, pacing, and shocking the connector also includes a right ventricular tip terminal (VR TIP) 52, a right ventricular ring terminal (VR RING) 54, a right ventricular shocking terminal (RV COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

The connector further includes notification leads 218, 219, and 220, which are configured for connection to an auxiliary or external notification unit (not shown).

At the core of ICD 10 is a programmable microcontroller 60, which controls the various modes of stimulation therapy. As is well known in the art, microcontroller 60 typically includes a microprocessor, or equivalent control circuitry, designed specifically for controlling the delivery of stimulation therapy and can further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design of microcontroller 60 are not critical. Rather, any suitable microcontroller 60 can be used to carry out the functions described herein. The use of microprocessor-based control circuits for performing timing and data analysis functions are well known in the art.

Representative types of control circuitry that may be used include the microprocessor-based control system of U.S. Pat. No. 4,940,052 (Mann et. al.) and the state-machines of U.S. Pat. Nos. 4,712,555 (Thornander et al.) and 4,944,298 (Sholder). For a more detailed description of the various timing intervals used within ICDs, and their inter-relationship, see U.S. Pat. No. 4,788,980 (Mann et. al.). The '052, '555, '298 and '980 patents are incorporated herein by reference.

Microcontroller 60 includes a timing control circuitry 79, which is used to control pacing parameters (e.g., the timing of stimulation pulses, the burst pacing parameters, etc.) as well as to keep track of the timing of refractory periods, post ventricular atrial refractory period (PVARP) intervals, noise detection windows, evoked response windows, alert intervals, marker channel timing, etc., which are well known in the art. Examples of pacing parameters include, but are not limited to, atrio-ventricular (AV) delay, interventricular (RV-LV) delay, atrial interconduction (A-A) delay, ventricular interconduction (V-V) delay, and pacing rate.

Microcontroller 60 utilizes arrhythmia detection circuitry 75, fibrillation type detector 210, and morphology detection circuitry 76 to recognize and classify AF by type; i.e. Type I AF, Type II AF, Type III AF, or Type IV AF. More specifically, fibrillation type detector 210 processes the EGM collected by the ICD, analyzes the EGM morphologies, and thereafter classifies the EGM by type, under the Wells classifications discussed above.

Microcontroller 60 further includes a therapy selector 212. The therapy selector 212 is configured and programmed to receive input from the fibrillation type detector 210 and thereafter select the appropriate therapy. The appropriate therapy can be selected from a plurality of therapies. For example, an ATP therapy can be used. Alternative therapies include a hybrid therapy including a combination of ATP therapy and drug therapy, shock therapy, or any other electrotherapies known in the art.

As shown in FIG. 4, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70 and 72 may include dedicated, independent pulse generators, multiplexed pulse generators, or shared pulse generators. Pulse generators 70 and 72 are controlled by microcontroller 60 via appropriate control signals 76 and 78, respectively, to trigger or inhibit the stimulation pulses.

Switch 74 includes a plurality of switches for connecting the desired electrodes to the appropriate I/O circuits, thereby providing complete electrode programmability. Accordingly, switch 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch 74 determines the "sensing polarity" of the cardiac signal by selectively closing the appropriate switches, as is also known in the art. In this way, a clinician may program the sensing polarity independent of the stimulation polarity.

Each sensing circuit, 82 and 84, employs one or more low power, precision amplifiers with programmable gain and/or automatic gain control, bandpass filtering, and a threshold detection circuit, as known in the art, to selectively sense the cardiac signal of interest. The automatic gain control enables ICD 10 to deal effectively with the difficult problem of sensing the low amplitude signal characteristics of atrial or ventricular fibrillation. Such sensing circuits, 82 and 84, can be used to determine cardiac performance values.

The outputs of atrial and ventricular sensing circuits 82 and 84 are connected to microcontroller 60, which in turn is able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 86.

For arrhythmia detection, ICD 10 utilizes the atrial and ventricular sensing circuits 82 and 84 to retrieve EGM signals from the heart. The AF is then classified by morphology detector 76 and fibrillation type detector 210, by comparing the EGM morphologies to those of predefined AF types, in order to determine the type of remedial therapy that is needed (e.g., ATP, bradycardia pacing, cardioversion shocks, burst pacing therapy, a hybrid therapy including a combination of ATP therapy and drug therapy, or defibrillation shock therapy, collectively referred to as "tiered therapy").

Cardiac signals are also applied to the inputs of an analog-to-digital (A/D) data acquisition system 90. Data acquisition system 90 is configured to acquire intracardiac electrogram signals, convert the raw analog data into a digital signal, and store the digital signals for later processing and/or telemetric transmission to an external device 102. Data acquisition system 90 is coupled to right atrial lead 20, coronary sinus lead 24, and right ventricular lead 30 through switch 74 to sample cardiac signals across any pair of desired electrodes.

Advantageously, data acquisition system 90 can be coupled to microcontroller 60, or other detection circuitry, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90 via a control signal 92 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Kleks et. al.), which patents are hereby incorporated herein by reference. The type of capture detection system used is not critical.

Microcontroller 60 is further coupled to a memory 94 by a suitable data/address bus 96, wherein the programmable operating parameters used by microcontroller 60 are stored and modified, as required, in order to customize the operation of ICD 10 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to heart 12 within each respective tier of therapy.

Advantageously, the operating parameters of ICD 10 may be non-invasively programmed into memory 94 through telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 advantageously allows intracardiac electrograms and status information relating to the operation of ICD 10 (as contained in microcontroller 60 or memory 94) to be sent to external device 102 through established communication link 104. For examples of such external devices, see U.S. Pat. No. 4,809,697 (Causey, III et al.); U.S. Pat. No. 4,944,299 (Silvian); and U.S. Pat. No. 6,275,734 (McClure et al.); all patents being hereby incorporated herein by reference. In an alternative embodiment, telemetry circuit 100 may be used to transmit notification signals to an external drug delivery device.

ICD 10 further includes a physiologic sensor 108 that can be used to detect changes in cardiac performance or changes in the physiological condition of the heart. Accordingly, microcontroller 60 can respond by adjusting the various pacing parameters (such as amplitude, rate, AV Delay, RV-LV Delay, V-V Delay, etc.). Microcontroller 60 controls adjustments of pacing parameters by, for example, controlling the stimulation pulses generated by the atrial and ventricular pulse generators 70 and 72. While shown as being included within ICD 10, it is to be understood that physiologic sensor 108 may also be external to ICD 10, yet still be implanted within or carried by the patient. More specifically, sensor 108 can be located inside ICD 10, on the surface of ICD 10, in a header of ICD 10, or on a lead (which can be placed inside or outside the bloodstream).

ICD 10 further includes a magnet detection circuitry (not shown), coupled to microcontroller 60. It is the purpose of the magnet detection circuitry to detect when a magnet is placed over ICD 10. A clinician may use the magnet to perform various test functions of ICD 10 and/or to signal microcontroller 60 that the external programmer 102 is in place to receive or transmit data to microcontroller 60 through telemetry circuit 100.

As further shown in FIG. 4, ICD 10 is shown as having an impedance measuring circuit 112, which is enabled by microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to switch 74 so that any desired electrode may be used. The impedance measuring circuit 112 is not critical, and is shown only for completeness.

In the case where ICD 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 60 further controls a shocking circuit 16 by way of a control signal 18. The shocking circuit 16 generates shocking pulses of low (up to about 0.5 Joules), moderate (about 0.5-10 Joules), or high energy (about 11 to 40 Joules), as controlled by microcontroller 60. Such shocking pulses are applied to the patient's heart 12 through at least two shocking electrodes (e.g., selected from left atrial coil electrode 28, RV coil electrode 36, and SVC coil electrode 38). As noted above, housing 40 may act as an active electrode in combination with RV electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of about 5-40 Joules), delivered asynchronously (since R-waves may be too disorganized to be recognized), and pertaining exclusively to the treatment of fibrillation. Accordingly, microcontroller 60 is capable of controlling the synchronous or asynchronous delivery of the shocking pulses.

ICD 10 additionally includes a battery 110, which provides operating power to a load that includes all of the circuits shown in FIG. 4.

FIGS. 5A-5D show examples of electrogram signals classified as Type I AF, Type II AF, Type III AF, and Type IV AF, respectively. As evidenced by the diagrams, Type I AF represents discrete organized atrial EGMs with intervening isoelectric lines free of perturbation. Type II AF also represents discrete organized atrial EGMs, but without clear isoelectric intervals. Type III AF has disorganized atrial EGMs, without clear isoelectric intervals. Type IV AF is characterized as alternations between Type I AF and Type III AF.

Figure 6:
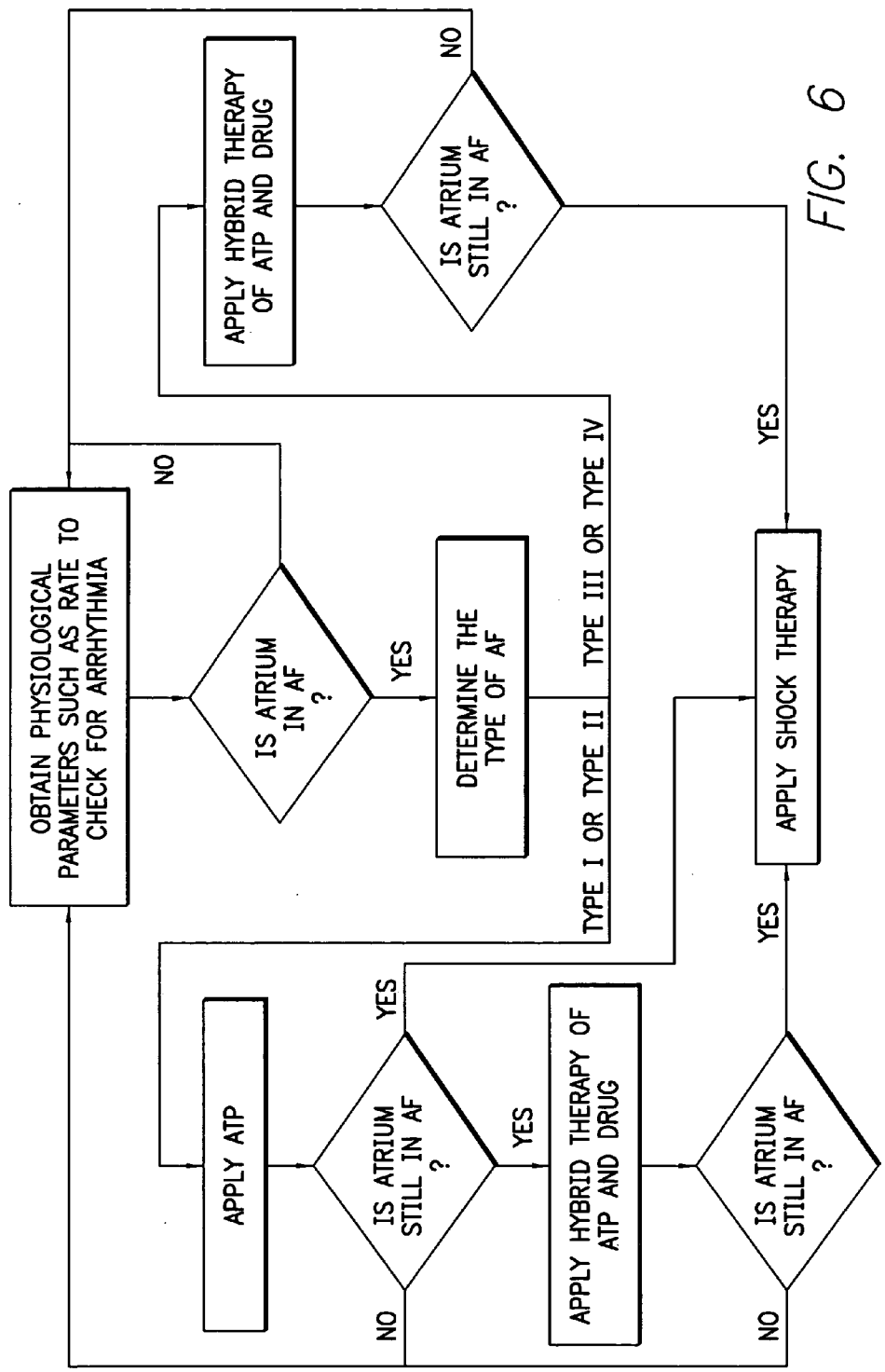
FIG. 6 is a flowchart showing a method of treating AF.

FIG. 6 is a flowchart showing a method of treating AF in accordance with an example embodiment. The first step of the method is to monitor the heart through ICD 10, obtaining EGM signals and physiological parameters, such as rate, to check for the onset of an arrhythmia. The next step is to determine if the heart is in AF, via the described sensing means. If the heart is not in AF, the ICD continues to monitor the heart until AF is detected. When AF is detected, ICD determines and classifies the AF by type, via the described means for classifying AF. If Type I AF or Type II AF is determined, the therapy selector in the ICD selects the appropriate pacing therapy, which is then initiated by the therapy circuit. The appropriate pacing therapy for Type I AF or Type II AF can be a standard pacing therapy; for example ATP therapy. If Type III AF or Type IV AF is determined, the therapy selector selects an appropriate therapy, generally a hybrid therapy including combination of ATP therapy and drug therapy. The ICD then continues to monitor the heart during the delivery of the appropriate therapy. In one embodiment, the ICD includes means for determining whether AF continues in the heart, such means can include a recurring loop of the sensing and detecting means described above.

If AF is successfully terminated, the appropriate therapy is ceased. If, however, it is determined that AF was not successfully terminated, the therapy selection unit in the ICD is configured to switch to a more aggressive therapy. For example, if the originally selected therapy was ATP therapy, a more aggressive therapy would be a hybrid therapy including a combination of ATP therapy and drug therapy. If AF is still not successfully terminated, a still more aggressive therapy can be applied. A more aggressive therapy than the hybrid therapy would be shock therapy. Alternatively, if the originally selected therapy was a hybrid therapy, a more aggressive therapy would be shock therapy.

CONCLUSION

Example embodiments of the methods, systems, and components have been described herein. As noted elsewhere, these example embodiments have been described for illustrative purposes only, and are not limiting. Other embodiments are possible and are covered by the following claims. Such embodiments will be apparent to persons skilled in the relevant art(s) based on the teachings contained herein.

What is claimed is:

1. A method of treating atrial fibrillation comprising:
(a) sensing activity of a heart;
(b) analyzing the activity to detect atrial fibrillation in the heart;
(c) classifying the atrial fibrillation as one of a plurality of atrial fibrillation types including:
Type I, wherein Type I comprises discrete organized atrial EGMs with intervening isoelectric lines free of perturbation;
Type II, wherein Type II comprises discrete organized atrial EGMs without clear isoelectric intervals;
Type III, wherein Type III comprises disorganized atrial EGMs without clear isoelectric intervals; and
Type IV, wherein Type IV is characterized as alternations between Type I and Type III;
(d) selecting a therapy from a plurality of therapies, wherein the therapy for Type I and Type II atrial fibrillation is ATP therapy, and the therapy for Type III and Type IV atrial fibrillation is a hybrid therapy, wherein the hybrid therapy is a combination of ATP therapy and drug therapy; and
(e) delivering the selected therapy to the heart.

2. The method of claim 1, wherein when drug therapy is selected in step (d), step (e) comprises delivering a drug to the heart, the drug being selected from a group consisting of: class I drugs, class III drugs, and dofetilide.

3. The method of claim 1, further comprising:
(f) determining if the selected therapy was successful in terminating the atrial fibrillation; and
(g) delivering a more aggressive therapy to the heart than in step (e) if the selected therapy was unsuccessful.

4. The method of claim 3, wherein when step (e) comprises delivering a hybrid therapy to the heart, step (g) comprises delivering shock therapy to the heart.

5. The method of claim 3, wherein when step (e) comprises delivering ATP therapy to the heart, step (g) comprises delivering shock therapy to the heart.

6. An implantable cardiac device comprising:
means for detecting atrial fibrillation;
means for classifying the atrial fibrillation as one of a plurality of atrial fibrillation including:
Type I, wherein Type I comprises discrete organized atrial EGMs with intervening isoelectric lines free of perturbation;
Type II, wherein Type II comprises discrete organized atrial EGMs without clear isoelectric intervals;
Type III, wherein Type III comprises disorganized atrial EGMs without clear isoelectric intervals; and
Type IV, wherein Type IV is characterized as alternations between Type I and Type III;
means for selecting a therapy from a plurality of therapies, wherein the therapy for Type I and Type II atrial fibrillation is ATP therapy, and the therapy for Type III and Type IV atrial fibrillation is a hybrid therapy, wherein the hybrid therapy is a combination of ATP therapy and drug therapy; and
means for delivering the selected therapy to the heart.

7. The implantable cardiac device of claim 6, further comprising:
means for determining if the selected therapy successfully terminated the atrial fibrillation;
means for selecting a more aggressive therapy if the selected therapy was not successful in terminating the atrial fibrillation; and
means for delivering the more aggressive therapy to the heart.

8. The implantable cardiac device of claim 7, wherein when the selected therapy is ATP therapy, the more aggressive therapy is the hybrid therapy.

9. The implantable cardiac device of claim 7, wherein when the selected therapy is a hybrid therapy, the more aggressive therapy is shock therapy.

10. The implantable cardiac device of claim 7, wherein when the selected therapy is ATP therapy, the more aggressive therapy is shock therapy.

11. The implantable cardiac device of claim 6, further comprising means for notifying the patient of the need to receive administration of a drug, wherein the drug is selected from a group consisting of: class I drugs, class III drugs, and dofetilide.

12. An implantable cardiac device comprising:
a sense circuit to sense activity of a heart;
a processor coupled to the sense circuit to analyze the activity and detect atrial fibrillation of the heart, classify the atrial fibrillation by type, including:
Type I, wherein Type I comprises discrete organized atrial EGMs with intervening isoelectric lines free of perturbation;
Type II, wherein Type II comprises discrete organized atrial EGMs without clear isoelectric intervals;
Type III, wherein Type III comprises disorganized atrial EGMs without clear isoelectric intervals; or
Type IV, wherein Type IV is characterized as alternations between Type I and Type III; and select a therapy based on the designated type; and
a therapy circuit, responsive to the processor, to deliver the selected therapy to the heart.

13. The implantable cardiac device of claim 12, wherein the selected therapy is selected from a group consisting of: ATP therapy, a hybrid therapy, and shock therapy.

14. The implantable cardiac device of claim 12, wherein the processor is configured to determine if the selected therapy successfully terminated the atrial fibrillation and the therapy circuit is configured to switch to a more aggressive therapy if the selected therapy was not successful in terminating atrial fibrillation in the heart.

15. A method of treating atrial fibrillation comprising:
sensing activity of a heart;
analyzing the activity;
detecting atrial fibrillation of the heart;
classifying the atrial fibrillation by type, including:
Type I, wherein Type I comprises discrete organized atrial EGMs with intervening isoelectric lines free of perturbation;
Type II, wherein Type II comprises discrete organized atrial EGMs without clear isoelectric intervals;
Type III, wherein Type III comprises disorganized atrial EGMs without clear isoelectric intervals; or
Type IV, wherein Type IV is characterized as alternations between Type I and Type III;
selecting a therapy based on the designated type; and
delivering the selected therapy to the heart.

* * * * *